United States Patent
Alvensleben

(10) Patent No.: US 9,827,362 B2
(45) Date of Patent: Nov. 28, 2017

(54) DIALYSIS SYSTEM COMPRISING HEAT RECOVERY

(71) Applicant: B. BRAUN AVITUM AG, Melsungen (DE)

(72) Inventor: Oliver Alvensleben, Hamburg (DE)

(73) Assignee: B. BRAUN AVITUM AG, Melsungen (DE)

( * ) Notice: Subject to any disclaimer, the term of this patent is extended or adjusted under 35 U.S.C. 154(b) by 229 days.

(21) Appl. No.: 14/333,175

(22) Filed: Jul. 16, 2014

(65) Prior Publication Data

US 2015/0021248 A1    Jan. 22, 2015

(30) Foreign Application Priority Data

Jul. 18, 2013   (DE) .................. 10 2013 107 673

(51) Int. Cl.
*A61M 1/16*    (2006.01)

(52) U.S. Cl.
CPC ........ *A61M 1/1662* (2014.02); *A61M 1/1664* (2014.02); *A61M 1/1672* (2014.02); *A61M 1/1686* (2013.01); *A61M 2202/04* (2013.01); *A61M 2202/0413* (2013.01); *A61M 2205/15* (2013.01); *A61M 2205/3334* (2013.01); *A61M 2205/3368* (2013.01); *A61M 2205/366* (2013.01); *A61M 2205/75* (2013.01)

(58) Field of Classification Search
CPC .............. A61M 1/1662; A61M 1/1664; A61M 1/1672; A61M 1/1686; A61M 2202/04; A61M 2202/0413; A61M 2205/15; A61M 2205/3334; A61M 2205/3368; A61M 2205/366; A61M 2205/75

See application file for complete search history.

(56) References Cited

U.S. PATENT DOCUMENTS

| 4,351,731 A | 9/1982 | Perrot |
| 4,715,959 A * | 12/1987 | Allan ..................... A61M 1/16 |
| | | 210/321.71 |
| 4,804,474 A | 2/1989 | Blum |

(Continued)

FOREIGN PATENT DOCUMENTS

| CN | 202161595 U | 3/2012 |
| CN | 102526822 A | 7/2012 |

(Continued)

OTHER PUBLICATIONS

German Search Report for DE 10 2013 107 673.4 dated Mar. 25, 2014.

(Continued)

*Primary Examiner* — Dirk Bass
(74) *Attorney, Agent, or Firm* — RatnerPrestia

(57) ABSTRACT

Dialysis systems including a water treatment unit preferably of the osmosis type, a drain line, and a heat exchanger are disclosed. A water supply line is connected to an outlet of the water treatment unit. The water supply line includes branch connections to which dialyzers are selectively fluid-coupled. Used-up dialysis fluid can be discharged from fluid-coupled dialyzers through the drain line. The heat exchanger, which is external to the dialyzers, connected on one side to the water supply line directly upstream of the branch connections and on the other side to the drain line.

16 Claims, 1 Drawing Sheet

(56) References Cited

U.S. PATENT DOCUMENTS

| | | | |
|---|---|---|---|
| 2011/0192796 A1 | 8/2011 | Smejtek et al. | |
| 2013/0056419 A1 | 3/2013 | Curtis | |
| 2013/0126430 A1* | 5/2013 | Kenley | B01D 61/00 210/638 |
| 2014/0014580 A1* | 1/2014 | Ritter | A61M 1/1656 210/636 |
| 2015/0021248 A1 | 1/2015 | Alvensleben | |

FOREIGN PATENT DOCUMENTS

| | | |
|---|---|---|
| CN | 204261115 U | 4/2015 |
| EP | 1 440 041 | 10/2009 |
| WO | WO 2012/119799 | 9/2012 |
| WO | WO 2012/175210 | 12/2012 |

OTHER PUBLICATIONS

European Search Report for EP14177209.5 dated Dec. 5, 2014.
Chinese Search Report for Chinese Application No. 201410344657, dated Apr. 28, 2017—9 Pages.

* cited by examiner

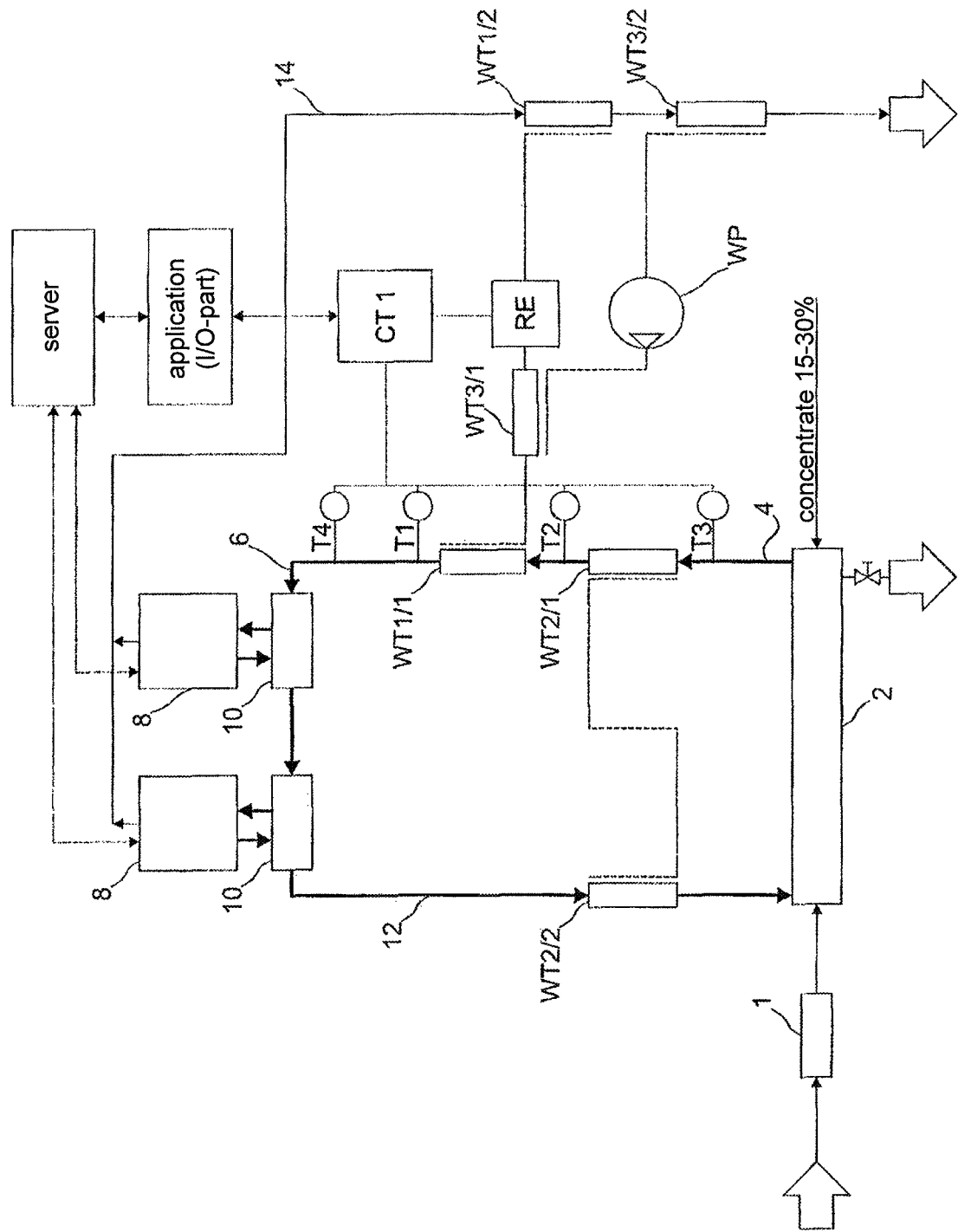

DIALYSIS SYSTEM COMPRISING HEAT RECOVERY

CROSS REFERENCE TO RELATED APPLICATIONS

This application claims priority to German application DE 10 2013 107 673.4 filed Jul. 18, 2013, the contents of such application being incorporated by reference herein.

FIELD OF THE INVENTION

The present invention relates to a dialysis system including heat recovery as well as central energy management and especially to a dialysis system consisting of a stationary water/fluid supply as well as dialysers selectively connectable thereto.

BACKGROUND

Dialysis systems of the relevant species in general comprise a stationary water supply including a number of tap options (tapping points) to which preferably mobile dialyzers can be selectively fluid-connected. Such dialyzers are equipped, inter alia, with internal heating systems so as to heat the water tapped off the stationary water supply to body temperature in the dialysis phase and to somewhat below boiling temperature (approx. 90° C.) in the disinfection phase. The primary energy required for this purpose is supplied to the dialyzers in the form of electrical power. In addition, each of the dialyzers can be provided with integrated heat exchangers to supply thermal energy in the used-up dialysis fluid to the water tapped off the stationary water supply and to the dialysis fluid freshly prepared therefrom and in this way to reduce the consumption of primary energy of the individual dialyzers.

These known concepts are thus substantially based on the principle of the isolated solution, as it is called, in the form of completely independently functioning dialyzers which each per se (individually) make available the required functional substances such as disinfectants or the dialysis fluid etc. each in the suited state (temperature, concentration) as well as each at proper points in time.

DESCRIPTION OF THE RELATED ART

As already indicated in the foregoing, in a dialysis treatment the dialysis fluid flowing through the dialyzer must be heated to a preset target temperature—usually about 37° C. In the dialyzer the incoming dialysis fluid/water is first preheated by the aforementioned internal heat exchanger and is subsequently heated, preferably electrically, to the target value by a heater. However, equipping each dialyzer with a heat exchanger is complicated and expensive. Depending on the number of connected dialyzers the entire dialysis system therefore becomes increasingly cost-intensive. Dispensing with the internal heat exchanger, however, would excessively increase the operating costs due to increasing primary energy consumption.

In WO 2012/175210 A2 an energy supply concept was suggested which basically provides the provision of inexpensively generated primary energy which is consumed, for example, in a dialysis center equipped with a dialysis system according to the afore-mentioned structural design. Accordingly, inter alia a photovoltaic system for generating electric power is paired with a heat pump especially for heating treatment rooms, the latter absorbing thermal energy from a drain line/pipe for used-up dialysis fluid and transfers useful energy into the treatment rooms. Thus the energy contained in the used-up dialysis fluid can be recycled by the heat pump. However, the principle of the isolated solution described in the beginning with respect to the individual dialyzers remains unaffected.

SUMMARY OF THE INVENTION

In view of this state of the art, an object is to provide an energy supply concept for a dialysis center by which the overhead of the dialysis center can be reduced in total.

Aspects of the present invention are based on the following energy-related considerations:

The improvement of the operating efficiency of a dialysis center is not only restricted to providing inexpensively generated primary energy and to recycling already used energy with known energy conversion systems, but also extends to the advantageous use thereof. For this purpose, it is necessary to analyze the monetary expenses in a dialysis center for acquisition, maintenance and current operation and to optimize them by properly centralizing the energies used.

It has turned out, for example, that especially in the case of dialyzers the individual equipment thereof with heat exchangers results in significant increases in costs especially for acquisition and maintenance (including disinfection). Although in parallel to this, the overhead for heating the dialysis center, for instance, can be reduced by alternative energy conversion systems according to the afore-mentioned prior art, the cost saving to be achieved thereby is inferior to the afore-mentioned cost increase according to findings of the present invention. Therefore, for business-management findings according to aspects of the invention it is beneficial to utilize the recycled thermal energy so that individual heat exchangers can possibly be dispensed with or can at least be dimensioned to be smaller.

According to recent findings, the individual operation of the dialyzers also may result in the fact that dialyzers are incidentally operated in equal operating phases, for example in a disinfection phase with high energy consumption. Thus temporary power consumption peaks are incurred which result in excessive electrical energy costs due to energy tariffs. The use of the possibly recycled primary energy accordingly should be configured and controlled so that coordination of the dialyzers which previously have been operated individually only is possible so as to avoid but at least reduce such consumption peaks.

In accordance with a first aspect of the present invention, which possibly has to be claimed independently, the dialysis system is equipped in its stationary section with a (central) water treatment unit preferably of the osmosis type to which fresh (tap) water or feed water is supplied and to the outlet of which a water supply pipe for (non-stationary) dialyzers is connected which has a section including a number of branch connections. Preferably mobile dialyzers are fluidly coupled or adapted to be coupled to these branch connections in a selective manner. As to their structure they substantially correspond to machines known from prior art, but they can also be designed without internal heat exchanger for energy recovery, where appropriate. Furthermore, the dialysis system includes a drain pipe through which used-up dialysis fluid can be cumulatively discharged from dialyzers fluidly coupled at the time in question into a drain or a collecting tank. In accordance with the invention, a (stationary/central) first heat exchanger (WT1) external to the dialyzer is provided the one side of which is connected to the water supply pipe between the water treatment device and a branch connection closest hereto in the flow direction and the pipe section including the branch connections, respectively, and the other side of which is connected to the discharge pipe and/or the collecting tank for the accumulated used dialysis fluid.

In other words, according to aspects of the present invention the water (permeate) is heated in the stationary section/zone of the system utilizing the thermal energy contained in the used-up dialysis fluid making use of a central heating, especially the first heat exchanger, and is made available to the dialyzers via the water supply pipe, preferably ring line. It is basically difficult in this context that when heating the feed water for osmosis the risk of microbic contamination in the water treatment unit is increased. Since further maximum temperature limits are usually applicable to osmosis diaphragms, the extent of heating of the feed water is limited and the dialyzers necessarily would have to electrically reheat. This would restrict the exploitation of the energy recovery.

However, according to aspects of the invention it is provided to preheat the already treated water (permeate) downstream of the treatment device so that increase in temperature of the osmosis diaphragm is avoided.

Preferably the water supply pipe constitutes a ring line which is returned to the water treatment device downstream of the number of branch connections in the form of a return pipe. Thus non-used already preheated water (permeate) is not lost, but is supplied to the first heat exchanger again via the water treatment device or directly downstream thereof for further preheating.

In addition, it may be provided that another temperature transfer means is arranged consisting of a second heat exchanger external to the dialyzer the one side of which is connected to the water supply pipe between the water treatment device and the first heat exchanger and the other side of which is connected to the return pipe between the water treatment device and a branch connection located most distant herefrom in the flow direction or the pipe section including the branch connections, respectively. Alternatively or in addition to this, a heat pump may be provided which absorbs thermal energy from the drain pipe and/or the return pipe and transfers useful energy to the water supply pipe between the water treatment device and the branch connection located closest hereto in the flow direction or the pipe section bearing the branch connections, respectively.

Hence, with the second heat exchanger preheating takes place while exploiting the residual energy in the water passed unused through the ring line, thereby the water returned to the treatment device cooling down and thus the treatment device (and the osmosis diaphragm provided therein) being prevented from heating. The heat pump offers the advantage that also the residual energy in the used dialysis fluid is still recycled so as to be fed into the water of the water supply pipe. In this case especially the heat pump is electronically controllable so as to increase the temperature of the water in the water supply pipe to an appropriate/desired value or else to reduce it (in this case the heat pump can be operated inversely as cooling device).

In accordance with another aspect of the present invention, which is possibly to be independently claimed, the dialysis system according to aspects of the invention is equipped with a central (stationary) electronic control unit to which at least one temperature sensor is connected for measuring the actual temperature in the water supply pipe at least between the first heat exchanger (WT1) and the pipe section including the branch connections, wherein the control unit accordingly controls a heat transfer controller in the area of the first heat exchanger and/or the heat pump for reaching a desired temperature, whereby the transferred or transferable amount of heat can be adjusted by the first heat exchanger and/or by the heat pump. Thus initially the water provided in the ring line can be basically prevented from overheating.

The central electronic control unit moreover is preferably electrically connected or connectable to the currently fluid-coupled dialyzers so as to obtain information about the current operating phases thereof and, as a function hereof, to control the heat transfer controller and/or the heat pump. This feedback permits energy management according to which the temperature of the water provided in the supply pipe/ring line is set to a value that minimizes the energy required for individually heating the water according to the individual operating phases of the dialyzers. For this purpose, it is beneficial when the desired temperature in the water supply pipe/ring line is set to the smallest one of the temperature values required by the currently connected dialyzers.

In accordance with another aspect of the present invention, which is possibly to be independently claimed, it may be provided that the electronic control unit directly/indirectly interferes with the operating cycle of the currently fluid-coupled dialyzers so as to coordinate the current operating phases thereof so that operating phases especially exhibiting high electric energy consumption are carried out staggered in time with minimum time overlapping. In this way power consumption peaks can be avoided/reduced so that the electric power can be purchased at a lower tariff.

BRIEF DESCRIPTION OF THE DRAWING

Hereinafter the invention will be explained in detail by way of a preferred embodiment with reference to the accompanying FIGURE. It shows the schematic fluid diagram of a dialysis system as well as the electronic control means for monitoring and controlling the fluid-mechanical elements of the dialysis system as well as for centrally coordinating the currently connected dialyzers and the current operating phases thereof, respectively.

DETAILED DESCRIPTION OF THE PREFERRED EMBODIMENTS

The dialysis system according to aspects of the present invention can be basically subdivided into a stationary area and a non-stationary/mobile area. The mobile area substantially relates to dialyzers which are optionally connectable to the stationary area separately from each other or can be taken into operation for carrying out a respective dialysis treatment on a patient. The stationary area inter alia includes a tubing system having fluid-related functional elements integrated therein (valves, throttles, filters etc.) for correctly supplying the dialyzers currently connected/provided in the operating state with purified/pretreated water as well as for discharging used-up fluids and a central control for providing water in a desired state (purified, heated, pressurized etc.) with functional elements suited for this (electronic control unit, temperature/pressure sensors, heat exchangers, heat pumps, pressure pumps etc.).

The dialyzers substantially correspond to prior art machines regarding their structure and function, but in the present invention they may be designed to include no heat exchangers at all or to include only a small internal heat exchanger. Moreover, the dialyzers include an electronic I/O interface via which the data/information relating to the respective current operating states/operating phases can be called in from the computer internal to the dialyzer (CPU) and control signals can be input for externally influencing the current operating states/operating phases. In so far the following description is primarily directed to the stationary area of the dialysis system according to aspects of the invention.

This area first comprises a feed water supply pipe 1 including an integrated filter, possibly water softener and possibly throttle, through which feed water is supplied from a feed water source (local water supply, water well etc.) to a water treatment unit 2, preferably osmosis filter plant at the inlet thereof in a pre-purified state and reduced to a particular pressure. In the water treatment unit 2 inter alia a water treatment is carried out so as to treat the feed water into water suited for dialysis. Water treatment units of this type are sufficiently known from prior art so that any further description is superfluous in this context.

A feed pipe 4 for water suited for dialysis which opens into a pipe section 6 having a number of connecting points 10 is connected to the outlet of said water treatment unit 2. Optionally dialyzers 8 according to the afore-mentioned design are fluid-connected to said connecting points (tap points) 10. The pipe section 6 including the number of connecting points 10 is transformed, viewed in the flow direction, into a return pipe 12 which is returned into the water treatment unit 2, especially at the inlet thereof. In this way a stationary ring line is resulting in which water suited for dialysis is permanently circulated and is repeatedly subjected to a cleaning process in the water treatment unit 2. Alternatively to this, it is basically also possible that the return pipe opens directly downstream of the water treatment unit into the feed pipe for water suited for dialysis (hereinafter only referred to as water feed pipe), wherein in this case purified water from the treatment plant is fed to the ring line only to such extent that volume tapped off the connecting points is replaced. Finally a pressure pump can be inserted in the water supply pipe and/or the return pipe so as to keep the water circulation going at a particular flow rate.

Furthermore, a collecting pipe 14 for used-up dialysis fluid preferably having a number of connecting points is provided to which the selected dialyzers 8 are connected so as to discharge used-up dialysis fluid through the collecting pipe 14 and dispose of the same in a drain or container. This collecting pipe 14 therefore shall be referred to hereinafter as waste water pipe or drain pipe.

In the water supply pipe 4 between the water treatment unit 2 and the pipe section 6 including the number of connecting points 10 a first stationary heat exchanger WT1 is interconnected at the one side WT1/1 thereof, and the other side WT1/2 thereof is interconnected in the drain pipe 14. In this way heat is removed from the fluid discharged in the drain pipe 14, is supplied to the water flowing in the water supply pipe 4 and this water is thus heated.

Preferably the first stationary heat exchanger WT1 can be electronically/electrically controlled with respect to its heat transfer capacity. For this purpose, the first stationary heat exchanger WT1 and the electric control means RE thereof, resp., is electrically connected to a central electronic control unit (CPU) CT1. Furthermore a number of temperature sensors T1-T4 are connected to the electronic control unit CT1 which are arranged in the flow direction spaced apart from each other at the water supply pipe 4 so that at least one temperature sensor is placed upstream and downstream of the first heat exchanger WT1. Preferably two temperature sensors T1, T4 are arranged downstream of the heat exchanger WT1 as well as spaced apart in the flow direction.

Between the first stationary heat exchanger WT1 and the water treatment unit 2 a second stationary heat exchanger WT2 is arranged the one side WT2/1 of which is interconnected into the water supply pipe 4 and the other side WT2/2 of which is interconnected into the return pipe 12. One of the temperature sensors T2 is provided at the water supply pipe 4 between the two heat exchangers WT1, WT2 and a further temperature sensor T3 is provided at the water supply pipe 4 between the second stationary heat exchanger WT2 and the water treatment unit 2. In this way the electronic control unit CT1 obtains information about the temperature course along the water supply pipe 4 starting from the treatment plant 2 to the pipe section 6 including the branch connecting points 10. Further the central electronic control unit CT1 is electrically connected to the dialyzers 8 currently fluid-connected to the ring line at the respective I/O interfaces thereof so as to obtain information about the current operating states/operating phases thereof and to interfere, where necessary, with the current operating states/operating phases thereof to control them corresponding to particular criteria in accordance with the following description.

Finally a stationary heat pump WP is provided which absorbs thermal (residual) energy from the drain pipe 14 and/or the return pipe 12 and transfers useful energy to the water supply pipe 4 between the water treatment unit 2 and the pipe section 6 including the branch connections 10. Concretely speaking, the heat pump WP absorbs still remaining thermal energy from the fluid flowing in the drain pipe 14 downstream of the first heat exchanger WT1 and gives off thermal energy into the water flowing in the water supply pipe 4 downstream of the second heat exchanger WT2 preferably in the area of the first heat exchanger WT1.

The functioning of the dialysis system according to aspects of the invention having the afore-described structure can be described as follows:

Basically in the dialysis system of the present invention feed water is purified in the water treatment unit 2 so that it obtains the quality suited for the following dialysis treatment. Subsequently the treated water is passed into the downstream ring line in which it flows from the water supply pipe 4 and the pipe section 6 including the branch connections 10 into the return pipe 12 and is returned from there to the water treatment unit 2 in accordance with a water circulation.

By flowing through the second heat exchanger WT2 directly downstream of the water treatment unit 2 the water in the water supply pipe 4 is first preheated in that thermal energy is withdrawn from the return pipe 12 and is transferred into the water supply pipe 4. In this way the water returned to the treatment plant 2 arrives there in the cold state so that an increase in temperature of an osmosis diaphragm, for example, in the treatment plant 2 is avoided.

After that the water flows in the water supply pipe 4 through the heat exchanger WT1 which now transfers thermal energy from the discharge pipe 14 conveying the used-up dialysis fluid into the water supply pipe 4 in a controlled manner. In addition, the heat pump WP is optionally operated which withdraws the residual energy in the used-up dialysis fluid not utilized by the first heat exchanger WT1 from the drain pipe 14 and feeds the same to the section of the water supply pipe 4 downstream of the first heat exchanger WT1. Alternatively, it is also possible to operate the heat pump WP inversely so as to cool the water in the ring line, for example in the case of a disinfection cycle in a dialyzer 8, whereupon the strongly heated dialyzer 8 must be cooled to the treatment temperature as quickly as possible.

Via the temperature sensors T1-T4 upstream of the second heat exchanger WT2, between the first and second heat exchangers as well as downstream of the second heat exchanger WT2 the temperature course can be measured along the water supply pipe 4, wherein the measuring results are supplied to the central control unit CT1. The latter also obtains information from the currently connected dialyzers 8 especially as to the current operating phase in which the individual dialyzer 8 is provided and which appropriate temperature the supplied water must have for this phase.

Based on this, the central control unit CT1 determines the respective lowest required temperature value as target value and regulates the water temperature via the first heat exchanger WT1 and/or the heat pump WP to this lowest value required on the side of all currently connected dialyzers 8. By the central heating and control the efficient preparation time of the individual dialyzers 8 is thus reduced. Moreover, the central control unit CT1 according to aspects of the invention offers further far-reaching control options:

In dialysis centers usually shifts are worked. The time course thus is similar and is continuously repeated. Since the dialyzers 8 basically must undergo a disinfection phase after a dialysis treatment, the total electric power required is increased in centers disproportionately high in a cyclic manner especially when plural dialyzers 8 simultaneously undergo the disinfection phase. Since utility companies also charge fees in dependence on the peak power required apart from the pure power consumption, it is reasonable to avoid or minimize such power peaks where possible.

The energy-intensive disinfection of a dialyzer in general takes place in the following steps:
rinsing dialysis fluid,
preheating,
sucking disinfectant,
heating disinfectant solution,
circulating hot solution,
rinsing hot solution,
cooling down dialyzer.

The heating capacity of each machine ranges from 1500 to 2000 W.

The central control unit CT1 obtains information, as indicated already in the foregoing, about the current operating phases of the connected dialyzers 8 and is adapted to interfere with the control internal to the dialyzer so that by time-shifted initiation of the afore-mentioned heating phase (for example within the range of approx. 15 minutes) the peak power required can be reduced (by about 20% vis-à-vis synchronized dialyzers). Based on the afore-mentioned communication between the central control unit CT1 and the respective connected dialyzers 8, with corresponding time-shifted heating phases also an equal time shift is resulting for the respective rinsing step, thereby also the maximum water quantity which is used for rinsing being reduced.

In the dialysis-free time the recirculation of the water in the ring line is maintained. Similarly to the refrigerator principle, a reduction of the temperature can result in reduced germ growth. By incorporating the heat pump WP into the dialysis system according to aspects of the invention in connection with the central control unit CT1 the water temperature in the ring line can be decreased to an appropriate low value. Furthermore, as already indicated in the foregoing, the heat pump WP can be used to cool the connected dialyzers 8 after the disinfection phase in a rapid and well-targeted manner.

By the communication between the stationary water supply (including water treatment unit) and the dialysis technology an interface is provided which results in further benefits apart from the afore-mentioned effects:

In the case of central disinfection an in-line hot cleaning can take place. Here not only the ring line (possibly including the water treatment unit) is disinfected but also the dialyzers are included. Via the central control unit an optimum inclusion of the dialyzers into the hot cleaning can be adjusted. This is done by a central control of the respective dialyzers after completion of the heating phase of the water supply. In this case the dialyzers are caused to start the suction phase of the central hot cleaning shifted in time so that the temperature in the supply pipe can be substantially maintained. The synchronization of this operation is thus carried out centrally by the control unit in contrast to the currently common practice according to which each machine has to be programmed individually.

Including the central control unit In the synchronization/coordination of the operating phase control entails increased safety. In the past numerous incidents/accidents have become known according to which hose couplings between the branch connections and the dialyzers detached independently or were damaged resulting in great damage by water in the dialysis center. With the aid of the central control unit a communication can take place between the individual dialyzers and the stationary water supply, however. The water supply and the control thereof receives data as to how many dialyzers are included in the hot cleaning, for example, and how much water has to be provided for this. Unless the ratio between the water passed into the ring line and the water returning into the water treatment unit is correct, the central control unit can conclude the presence of a leakage and e.g. automatically switch off the plant. Cost-intensive damage thus can be avoided.

Summing up, a dialysis system is disclosed comprising a water treatment unit preferably of the osmosis type at the outlet of which a water supply pipe is connected including a number of branch connections to which dialyzers are selectively fluid-coupled and comprising a drain pipe through which the used-up dialysis fluid from fluid-coupled dialyzers can be discharged. According to aspects of the invention, at least one heat exchanger external to the dialyzers is provided the one side of which is connected to the water supply pipe directly upstream of the branch connections and the other side of which is connected to the drain pipe.

The invention claimed is:

1. A dialysis system comprising:
An osmosis filter module configured to treat feed water received at an inlet to produce treated water suitable for dialysis, the osmosis filter module having an outlet connected to a first end of a supply line that opens into at least one line section provided with branch connections configured for connection to a plurality of dialyzers, the supply line configured to deliver the water suitable for dialysis to the plurality of dialyzers via the branch connections, and wherein the supply line has a second end connected to the inlet of the osmosis filter module and the supply line defines a ring line downstream of the at least one line section including the branch connections, through which unused water suitable for dialysis bypassing the branch connections is returned via the second end of the supply line to the inlet of the osmosis filter module, said second end of the supply line being configured as a return line;

A feed water supply pipe arranged between a feed water source and the osmosis filter module, the feed water supply pipe having an input connected to the feed water source and an output connected to the inlet of the osmosis filter module, for transporting the feed water to the osmosis filter module;

A drain line through which used dialysis fluid is discharged from the plurality of fluid-coupled dialyzers after passing through the plurality of dialyzers from the branch connections;

A first heat exchanger (WT1) external to the plurality of dialyzers having a first side (WT1/1) connected to the supply line between the outlet of the osmosis filter module and the line section including the branch connections and a second side (WT1/2) connected to the drain line, the first heat exchanger (WT1) configured to transfer heat from the used dialysis fluid in the drain line to the water suitable for dialysis in the supply line after exiting the outlet of the osmosis filter module; and A second heat exchanger (WT2) disposed externally to the plurality of dialyzers having one side (WT2/1) connected to the supply line between the outlet of the osmosis filter module and the first side (WT1/1) of the first heat exchanger (WT1), and a second side (WT2/2) connected to the return line between the inlet of the osmosis filter module and the line section including the branch connections, the second heat exchanger (WT2) configured to transfer heat from the unused water suitable for dialysis in the return line to the water suitable for dialysis in the supply line after exiting the outlet of the osmosis filter module, such that the unused water suitable for dialysis enters the inlet of the osmosis filter module unheated.

2. The dialysis system according to claim 1, the temperature transfer unit further comprising:
A heat pump arranged on at least one of the drain line or the return line to absorb thermal energy from the at least one of the drain line or the return line and to transfer heat to the supply line between the outlet of the osmosis filter module and the line section including the branch connections.

3. The dialysis system according to claim 2, wherein the heat pump is connected to the drain line downstream of the second side (WT1/2) of the first heat exchanger (WT1) and to the first side (WT1/1) of the first heat exchanger (WT1) to transfer the heat energy to the first side (WT1/1) of the first heat exchanger (WT1).

4. The dialysis system according to claim 2, wherein the heat pump is connected to the drain line downstream of the second side (WT1/2) of the first heat exchanger (WT1) and to the supply line immediately downstream of the first side (WT2/1) of the second heat exchanger (WT2) to transfer the heat energy to the water suitable for dialysis in the supply line after exiting the outlet of the osmosis filter module.

5. The dialysis system according to claim 2, further comprising a central electronic control unit to which at least one temperature sensor is connected which measures the actual temperature of the water suitable for dialysis in the supply line after exiting the osmosis filter at least between the first side (WT1/1) of the first heat exchanger (WT1) and the line section including the branch connections and which controls in accordance therewith a heat transfer controller and/or the heat pump so as to accomplish a target temperature of the water suitable for dialysis in the supply line, thereby the transferred or transferable heat quantity being adjustable by the first heat exchanger (WT1) and/or by the heat pump (WP).

6. The dialysis system according to claim 5, wherein the central electronic control unit is electrically connected to the dialyzers fluidly coupled at a first time so as to obtain information on the prevailing operating phases thereof and which, in accordance with this information, controls the heat transfer controller and/or the heat pump such that the target temperature of the water suitable for dialysis in the supply line upstream of the branch connections adjusts to the smallest value required by one of the currently connected dialyzers.

7. The dialysis system according to claim 6, wherein the electronic control unit intervenes in the operating sequence of the dialyzers fluidly coupled at the first time, so as to coordinate their prevailing operating phases such that operating phases with high electric power consumption are performed with a time shift to minimize temporal overlap.

8. The dialysis system of claim 1, wherein the osmosis treatment module is a reverse osmosis type water treatment unit.

9. The dialysis system of claim 1, further comprising:
a first fluid transport path in which the water suitable for dialysis passes through the line section after exiting the outlet of the osmosis filter module and through the branch connections to be used by the plurality of dialyzers, wherein the used dialysis fluid is discharged by the drain line; and
a second fluid transport path in which the water suitable for dialysis passes through the line section after exiting the outlet of the osmosis filter module and bypasses the branch connections without being used by the plurality of dialyzers to a return line, wherein the return line transports the unused water suitable for dialysis to the inlet of the osmosis filter module.

10. A method for improving energy efficiency of a dialysis center and recycling heat energy, the method comprising:
Transporting, with a feed water supply pipe having an input connected to a feed water source and an output connected to an inlet of an osmosis filter module, feed water from the feed water source to the inlet of the osmosis filter module;
Treating, with the osmosis filter module, the feed water to produce treated water suitable for dialysis;
Delivering, via an outlet of the osmosis filter module, the water suitable for dialysis to a first end of a supply line, the supply line opening into at least one line section provided with branch connections configured for connection to a plurality of dialyzers;
Delivering, with the supply line, the water suitable for dialysis to the plurality of dialyzers via the branch connections;
Discharging, with a drain line connected to the plurality of dialyzers, used dialysis fluid from the plurality of dialyzers after passing through the plurality of dialyzers from the branch connections;
Transferring, with a first heat exchanger (WT1) disposed externally to the plurality of dialyzers, heat from the used dialysis fluid in the drain line to the water suitable for dialysis in the supply line after the water suitable for dialysis exits the outlet of the osmosis filter module, wherein the first heat exchanger (WT1) has a first side (WT1/1) connected to the supply line between the outlet of the osmosis filter module and the line section including the branch connections and a second side (WT1/2) connected to the drain line;

Returning, to the inlet of the osmosis filter module with a second end of the supply line connected to the inlet of the osmosis filter module, unused water suitable for dialysis that bypasses the branch connections, wherein the supply line defines a ring line and the second end of the supply line defines a return line; and Transferring, with a second heat exchanger (WT2) disposed externally to the plurality of dialyzers, heat from the unused water suitable for dialysis in the return line to the water suitable for dialysis in the supply line after exiting the outlet of the osmosis filter module, such that the unused water suitable for dialysis enters the osmosis filter module via the inlet unheated; and wherein the second heat exchanger (WT2) has one side (WT2/1) connected to the supply line between the outlet of the osmosis filter module and the first side (WT1/1) of the first heat exchanger (WT1), and a second side (WT2/2) connected to the return line between the inlet of the osmosis filter module and the line section including the branch connections.

11. The method of claim 10, further comprising:

Absorbing, with a heat pump arranged on at least one of the drain line or the return line, thermal energy from the at least one of the drain line or the return line; and Transferring, with the heat pump, heat to the supply line between the outlet of the osmosis filter module and the line section including the branch connections such that the water suitable for dialysis in the supply line after exiting the outlet of the osmosis filter module is heated.

12. The method of claim 11, further comprising:

transferring, with the heat pump, the heat to the first side (WT1/1) of the first heat exchanger (WT1) from the drain line such that the water suitable for dialysis in the supply line after exiting the outlet of the osmosis filter module is heated, wherein the heat pump is connected to the first side (WT1/1) of the first heat exchanger (WT1) and to the drain line downstream of the second side (WT1/2) of the first heat exchanger (WT1).

13. The method of claim 11, further comprising:

transfer, with the heat pump, the heat to the supply line immediately downstream of the first side (WT2/1) of the second heat exchanger (WT2) from the drain line such that the water suitable for dialysis in the supply line after exiting the outlet of the osmosis filter module is heated, wherein the heat pump is connected to the drain line downstream of the second side (WT1/2) of the first heat exchanger (WT1) and to the supply line immediately downstream of the first side (WT2/1) of the second heat exchanger (WT2).

14. The method of claim 11, further comprising:

measuring, with a central electronic control unit to which at least one temperature sensor is connected, the actual temperature of the water suitable for dialysis in the supply line after exiting the outlet of the osmosis filter at least between the first side (WT1/1) of the first heat exchanger (WT1) and the line section including the branch connections; and controlling, with the central electronic control unit, at least one of a heat transfer controller or the heat pump to achieve a target temperature of the water suitable for dialysis in the supply line, thereby the transferred or transferable heat quantity being adjustable by at least one of the first heat exchanger (WT1) or the heat pump (WP).

15. The method of claim 14, wherein the central electronic control unit is electrically connected to the plurality of dialyzers, the method further comprising:

obtaining, with the central electronic control unit, information on prevailing operating phases of the plurality of dialyzers;

controlling, with the central electronic control unit in accordance with the obtained information, the at least one of the heat transfer controller or the heat pump; and adjusting, with the least one of the heat transfer controller or the heat pump, a target temperature of the water suitable for dialysis in the supply line upstream of the branch connections to the smallest value required by one of the plurality of currently connected dialyzers.

16. The method of claim 15, further comprising:

intervening, with the central electronic control unit, in operating sequences of the plurality of currently connected dialyzers at a first time to coordinate the prevailing operating phases of the plurality dialyzers such that operating phases with high electric power consumption are performed with a time shift to minimize temporal overlap.

* * * * *